(12) United States Patent
Treu et al.

(10) Patent No.: US 6,254,567 B1
(45) Date of Patent: Jul. 3, 2001

(54) FLOW-THROUGH PERITONEAL DIALYSIS SYSTEMS AND METHODS WITH ON-LINE DIALYSIS SOLUTION REGENERATION

(75) Inventors: Dennis M. Treu, Bedford, NH (US); Jeffrey H. Burbank, Boxford; James M. Brugger, Newburyport, both of MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 09/512,132

(22) Filed: Feb. 23, 2000

Related U.S. Application Data (60) Provisional application No. 60/121,733, filed on Feb. 26, 1999.

(51) Int. Cl.$^7$ .................................................. A61M 1/00
(52) U.S. Cl. ............................................................ 604/29
(58) Field of Search ................................. 604/5.01, 4.01, 604/31, 27, 28, 29, 317, 322, 323, 326, 327, 328, 332, 335; 210/645–647

(56) References Cited

U.S. PATENT DOCUMENTS

| | | |
|---|---|---|
| 5,645,734 | 7/1997 | Kenley et al. . |
| 5,762,782 | 6/1998 | Kenley et al. . |

*Primary Examiner*—Manuel Mendez
(74) *Attorney, Agent, or Firm*—Ryan Kromholz & Manion, S.C.

(57) ABSTRACT

Peritoneal dialysis is performed by circulating peritoneal dialysis solution through a peritoneal cavity by conveying peritoneal dialysis solution through an inlet branch into the peritoneal cavity and by withdrawing peritoneal dialysis solution through an outlet branch from the peritoneal cavity. Peritoneal dialysis solution in the outlet branch is conveyed along a first side of a porous membrane while conveying a regeneration solution containing at least one regenerating agent along a second side of the porous membrane. The membrane is configured to transport the regenerating agent into the peritoneal dialysis solution while transporting waste from the peritoneal dialysis solution into the regeneration solution, thereby creating a regenerated peritoneal dialysis solution. The regenerated peritoneal dialysis solution is circulated through the inlet branch into the peritoneal cavity.

59 Claims, 6 Drawing Sheets

FLOW-THROUGH PERITONEAL DIALYSIS SYSTEMS AND METHODS WITH ON-LINE DIALYSIS SOLUTION REGENERATION

RELATED APPLICATION

This application is a continuation-in-part of U.S. Provisional Patent Application Serial No. 60/121,733, filed Feb. 26, 1999, and entitled "Flow-Through Peritoneal Dialysis Systems and Methods with On-Line Dialysis Solution Regeneration," which is incorporated herein by reference.

1. Field of the Invention

The invention relates to systems and methods for performing peritoneal dialysis.

BACKGROUND OF THE INVENTION

Peritoneal Dialysis (PD) periodically infuses sterile aqueous solution into the peritoneal cavity. This solution is called peritoneal dialysis solution, or dialysate. Diffusion and osmosis exchanges take place between the solution and the bloodstream across the natural body membranes. These exchanges remove the waste products that the kidneys normally excrete. The waste products typically consist of solutes like sodium and chloride ions, and the other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During CAPD, the patient drains spent peritoneal dialysis solution from his/her peritoneal cavity. The patient then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

Still, CAPD and APD as practiced today require the use of bagged solutions, which are expensive and difficult to handle and connect. Bagged solutions also do not permit the use of bicarbonate buffering solutions due to sterilization issues. The complexity and size of past machines and associated disposables for various APD modalities have dampened widespread patient acceptance of APD as an alternative to manual peritoneal dialysis methods.

SUMMARY OF THE INVENTION

The invention provides systems and methods for conducting peritoneal dialysis.

One aspect of the invention provides a system for conducting peritoneal dialysis. The system comprises a pumping assembly to circulate peritoneal dialysis solution through a peritoneal cavity to perform peritoneal dialysis. The pumping assembly includes an inlet branch to convey peritoneal dialysis solution into the peritoneal cavity and an outlet branch to withdraw peritoneal dialysis solution from the peritoneal cavity. The system also includes a regeneration assembly coupled in-line between the inlet and outlet branches. The regeneration assembly includes a source of a regeneration solution that carries at least one agent for regenerating spent peritoneal dialysis solution. The regenerating agent can include, e.g., an electrolyte and a buffering agent. The regeneration assembly also includes a porous membrane having a first side and a second side. The pumping assembly circulates peritoneal dialysis solution along the first side of the porous membrane from the outlet branch to the inlet branch. The regeneration solution is circulated along the second side of the porous membrane. The porous membrane is configured to transport waste from spent peritoneal dialysis solution into the regeneration solution and to transport the regenerating agent from the regeneration solution into spent peritoneal dialysis solution. The transport can occur, e.g., by diffusion, convection, or both. The regeneration assembly thereby operates to create from peritoneal dialysis solution in the outlet branch, a regenerated dialysis solution for conveyance through the inlet branch into the peritoneal cavity.

The source of regeneration solution can draw water from a source of water, which can comprise, e.g., running tap water. In one embodiment, the source of regeneration solution includes a device to treat water drawn from the source of water, as well as a device to mix the at least one regenerating agent with water drawn from the source of water.

The source of regeneration solution can alternatively include a container holding a volume of water in which the at least one regenerating agent is mixed. In one embodiment, the source of regeneration solution includes a first container holding a volume of water and a second container that holds the at least one regenerating agent. The second container is located within the first container. The second container includes a wall material that, when contacted by water, transports the at least one regenerating agent into the water, thereby forming the regeneration solution.

In one embodiment, the regeneration assembly includes a device to heat the regeneration solution before circulation along the second side of the porous membrane.

In one embodiment, the inlet branch communicates with a first access device providing access to the peritoneal cavity, and the outlet branch communicates a second access device providing access to the peritoneal cavity independent of the access provided by the first device. In this arrangement, the pumping assembly can include a controller that withdraws peritoneal dialysis solution through the second access device into the regeneration assembly while conveying regenerated peritoneal dialysis solution from the regeneration device into the peritoneal cavity through the first access device. At least one of the first and second access devices can comprise, e.g., a subcutaneous access port.

In one embodiment, the inlet and outlet branches jointly communicate with a single access device that provides common access to the peritoneal cavity. In this arrangement, the pumping assembly can include a controller operating in a draw mode, to withdraw peritoneal dialysis solution from the peritoneal cavity through the single access device into the regeneration assembly, and a return mode, to convey regenerated peritoneal dialysis solution into the peritoneal cavity through the single access device. The single access device comprises, e.g., a subcutaneous access port.

In one embodiment, the regeneration assembly includes a fluid balancing module to maintain a volumetric balance between waste and regenerating agent transported by the porous membrane.

In one embodiment, the regeneration assembly includes an ultrafiltration module to selectively transport a preselected greater volume of waste than regenerating agent.

In one embodiment, the pumping assembly can accommodate circulation of a cleaning or disinfecting agent through the inlet and outlet branches, bypassing the peritoneal cavity. The regeneration assembly can also accommodate circulation of a cleaning or disinfecting agent along the first and second sides of the porous membrane.

Another aspect of the invention provides a method for conducting peritoneal dialysis. The method (i) circulates peritoneal dialysis solution through a peritoneal cavity to perform peritoneal dialysis by conveying peritoneal dialysis solution through an inlet branch into the peritoneal cavity and by withdrawing peritoneal dialysis solution through an outlet branch from the peritoneal cavity. During at least a portion of step (i), the method(ii) conveys peritoneal dialysis solution in the outlet branch along a first side of a porous membrane while conveying a regeneration solution containing at least one regenerating agent along a second side of the porous membrane. The membrane is configured to transport the regenerating agent into the peritoneal dialysis solution while transporting waste from the peritoneal dialysis solution into the regeneration solution, thereby creating a regenerated peritoneal dialysis solution. During at least a portion of step (i), the method (iii) circulates the regenerated peritoneal dialysis solution through the inlet branch into the peritoneal cavity.

The steps (ii), and (iii) can be performed simultaneously or sequentially.

During step (ii), a prescribed volumetric balance can be maintained between waste and regenerating agent transported by the porous membrane to achieve fluid balancing. Also during step (ii), a preselected greater volume of waste than regenerating agent cen be selectively transported by the porous membrane to achieve ultrafiltration. $$

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. System Overview

Figure 1:
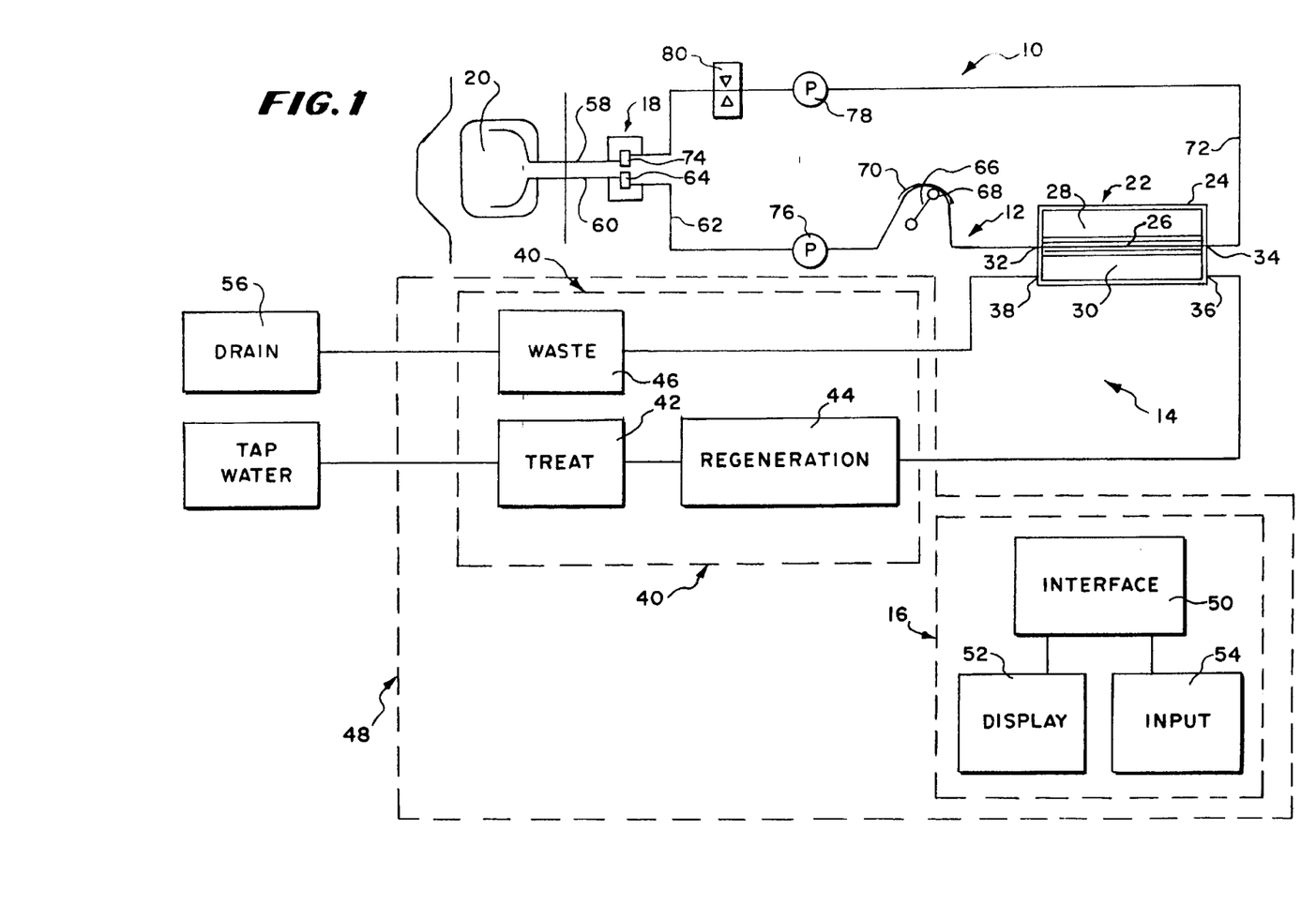
FIG. 1 is a schematic view of a system for conducting flow-through peritoneal dialysis, showing a dual access with the peritoneal cavity.

FIG. 1 shows a system 10 for conducting flow-through peritoneal dialysis, which embodies the features of the invention. The system 10 includes a peritoneal dialysis solution flow set 12 that is connected to an access device 18. The access device 18 establishes communication between the system 10 and the peritoneal cavity 20 of a patient.

The system 10 also includes a cycler 14. The cycler 14 interacts with the flow set 12, to pump peritoneal dialysis solution into and out of the patient's peritoneal cavity 20.

The system 10 also includes a controller 16. The controller 16 governs the interaction between the set 12 and the cycler 14, to perform a selected flow-through peritoneal dialysis procedure.

The flow set 12 includes an in-line membrane device 22. The membrane device 22 includes a housing 24, which encloses a semipermeable membrane 26. The membrane 26 can encloses a semipermeable membrane 26. The membrane 26 can have different geometries. In the illustrated embodiment, the membrane 26 comprises a bundle of hollow fibers, through which peritoneal dialysis fluid drawn from the peritoneal cavity 20 of the patient flows.

The membrane 26 compartmentalizes the chamber 24 into a patient side 28 and a regeneration side 30. In the illustrated embodiment, the patient side 28 comprises the bores of the bundled hollow fibers, and the regeneration side 30 comprises the interior space surrounding the bundled hollow fibers. An inlet port 32 and an outlet port 34 convey dialysis solution into and out of the patient side 28 of the chamber 24 (i.e., into and out of the bores of the hollow fibers). An inlet port 36 and outlet port 38 convey regeneration solution into and out of the regeneration side 30 of chamber 24.

The set 12 circulates peritoneal dialysis solution, transported from the patient's peritoneal cavity 20, along the patient side 28 of the membrane 26. The set 12 also circulates a regeneration solution containing electrolytes and/or bicarbonate buffering materials along the regeneration side 30 of the membrane 26. The cycler 14 creates and supplies the regeneration solution, as will be described in detail later.

The pores of the membrane 26 are sized to pass, by diffusion and convection, waste and uremic toxins from the patient side 28 to the regeneration side 30. The pores of the membrane 26 are also sized to pass, by the same transport mechanisms, electrolytes and bicarbonate buffering materials from the regeneration side 30 to the patient side 28.

The in-line membrane device 22 thereby makes possible the continuous, on-line regeneration of peritoneal dialysis solution circulated in the set 12.

The cycler 14 includes a fluid source 40. In the embodiment shown in FIG. 1, the fluid source 40 comprises a water treatment module 42, a regeneration solution module 44, and a waste module 46.

The water treatment module 42 receives water from a household water supply and processes the water, using e.,g., filtration, or absorption, or filtration and absorption, or reverse osmosis (with or without pre-filtration and/or absorption), or de-ionization (with or without pre-filtration and/or absorption), or reverse osmosis and de-ionization (with or without pre-filtration and/or absorption). By such processing, the water treatment module 42 creates water substantially free of pyrogens and microorganisms.

The regeneration solution module 44 receives processed water from the water treatment module 42. The regeneration solution module 44 mixes electrolytes and/or buffering agents with the processed water to create the regeneration solution. The module 44 verifies the make up of the solution and heats the solution to body temperature, for delivery to the regeneration side 30 of the membrane device 22.

The waste module 46 directs system drain and waste water from the regeneration side 30 of the membrane device 22 to a drain 56 or other selected receptacle.

The fluid source 40 of the cycler 14 obviates the need for bagged solutions, except for initially priming the set 12 prior to conducting a flow-through peritoneal dialysis procedure. The fluid source 40 makes possible the continuous, on-line regeneration of peritoneal dialysis solution, which the set 12 circulates from and into the patient's peritoneal cavity 20.

The processing controller 16 can comprise a stand-alone micro-processor controlled module or a mechanically and/or electrically controlled module linked to the cycler 14. In the illustrated embodiment, however, the cycler 14 and controller 16 are located within a common housing 48. The housing 48 presents a compact footprint, suited for operation upon a table top or other relatively small surface normally found in the home.

In the illustrated embodiment, the controller 16 also includes an interactive user interface 50. The interface So comprises some form of a display 52, which can be analog or digital, and some form of a patient input device 54, such as knobs, dials, switches, keyboard or a touch screen on the display 52. The interface 50 can e.g., present on the display 52 the current status of the cycler 14, or prompt the user to input commands and information, or receive data from the various sensors and other components of the cycler 14, record the data in memory, or control the operation of the active components of the cycler 14 (such as valves, pumps, heaters, etc.), or alert the patient to abnormal or failure conditions in the cycler 14 with alarms or other indicators, or any or all of these functions. Additionally, the interface 50 can be linked, e.g., by modem, to a central monitoring station or a central data collection site.

The set 12 can be a single use, disposable item, or it can, with cleaning and disinfection, be reusable. This aspect with be described in greater detail later.

In use, the cycler 14 draws peritoneal dialysis solution from the patient's peritoneal cavity 20, regenerates the dialysis solution, and returns the regenerated dialysis solution to the patient's peritoneal cavity 20, in a continuous or semi-continuous, extracoporeal path. The constant or semi-constant flow of peritoneal dialysis solution through the peritoneal cavity 20 provides sustained, high clearance of waste and toxins, which are conveyed to the drain 56. The on-line regeneration of dialysis solution provides lower costs and requires less manipulation and set up than systems relying upon the connection and disconnection of bagged solutions.

II. Flow-Through Peritoneal Dialysis Modalities

The system 10 is particularly well suited to perform flow-through peritoneal dialysis (FTPD) . For this reason, the use of the system 10 to perform various modalities of FTPD will be described in detail.

(A) Dual Access to the Peritoneal Cavity

In the embodiment shown in FIG. 1, the access device 18 provides dual access, having a dedicated inlet 58 for conveying solution into the peritoneal cavity 20 and a dedicated outlet 60 for conveying solution from the peritoneal cavity 20. Dual access provides continuous flow into and out of the peritoneal cavity 20.

Dual access can be provided, e.g., by a two indwelling catheters, a dual lumen, indwelling catheter, or two subcutaneous access devices. Further details of a preferred subcutaneous access device will be provided later.

In this arrangement, the set 12 includes a flexible inlet tube 62 with a connector 64 that connects to the peritoneal cavity outlet 60. The inlet tube 62 also is also connected to the inlet port 32 on the patient side 28 of the membrane device 22, to convey dialysis solution across the patient side 28 of the membrane 26.

The cycler 14 includes an inlet pump 66. In the illustrated embodiment, the inlet pump 66 comprises a peristaltic pump. The pump 66 includes rotating rollers 68 driven by a motor, e.g., a brushless D.C. motor. The rollers 68, in succession, press against and pinch the flexible inlet tube 62 against a pump race 70, thereby urging liquid flow from the peritoneal cavity 20 through the inlet tube 62 across the patient side 28 of the membrane device 22 in known peristaltic fashion. Of course, other types of noninvasive pumps can be used, provided that pump speed can be monitored and controlled.

The set 12 further includes an outlet tube 72, which is coupled to the outlet port 34 of the patient side 28 of membrane device 22. The outlet tube 72 conveys regenerated dialysis solution from the patient side 28 of the membrane 26. The outlet tube 72 carries a connector 74 that couples to the peritoneal cavity inlet 58, to further convey the regenerated dialysis solution into the patient's peritoneal cavity 20.

The cycler 14 also includes two noninvasive pressure sensors 76 and 78. The sensors 76 and 78 monitor fluid pressure, respectively, in the inlet tube 62 and the outlet tube 72. The controller 16 analyzes the sensed pressures and regulates the inlet pump 66 to maintain the pressure in the outlet tube 72 within a predetermined safe range. The controller 16 also terminates operation of the inlet pump 66 if sensed pressure in the inlet tube 62 falls outside a predetermined range.

The cycler 14 further includes a noninvasive fluid intake valve 80. The controller 16 closes the intake valve 80, to prevent the supply of dialysis solution to the peritoneal cavity 20, should a predetermined alarm condition arise.

(B) Single Access to the Peritoneal Cavity

Figure 2:
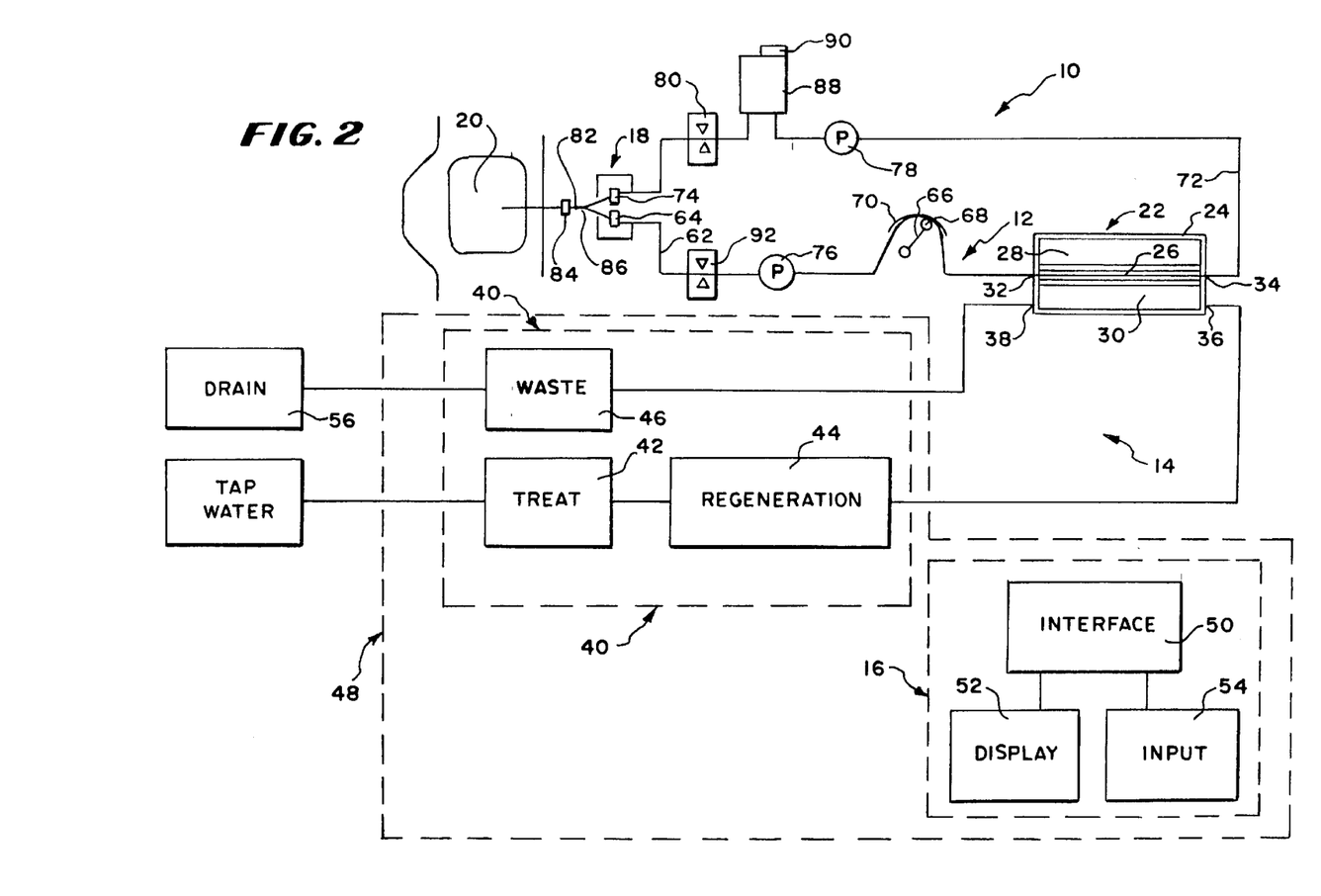
FIG. 2 is a schematic view of a system for conducting flow-through peritoneal dialysis, showing a single access with the peritoneal cavity.

In the embodiment shown in FIG. 2, the access device 18 provides a single access through a single indwelling catheter or a single subcutaneous access device. The single access arrangement provides semi-continuous flow of dialysis solution into and out of the peritoneal cavity 20 in a succession of draw modes and return modes. The quick cycling of draw and return modes provides virtually the same results as a continuous flow-through procedure, as just described.

In this arrangement, the set 12 includes a connector tube 82 with a connector 84 that connects to the single access device 18. The connector tube 82 includes a y-connector 86, to which the inlet tube 62 and the outlet tube 72 are connected. The inlet tube 62 is connected to the inlet port 32 of the membrane device 22. The outlet tube 72 is coupled to the outlet port 34 of the membrane device 22.

In this arrangement, the outlet tube 72 includes an in-line, non-vented reservoir 88. The reservoir 88 receives regenerated dialysis solution from the membrane device 22. A sensor 90 monitors fluid pressure in the reservoir 88, which increases as solution fills the reservoir 88 and decreases as solution exits the reservoir 88.

The cycler 14 includes in the outlet tube 72 the same, previously described noninvasive fluid intake valve 80. In the arrangement, the cycler 14 also includes a noninvasive fluid removal valve 92 in the inlet tube 62.

The controller 16 toggles the fluid intake valve 80 and the fluid removal valve 92 between opposing opened and closed states, to affect successive fluid draw and fluid return modes.

In the fluid draw mode, the fluid removal valve 92 is opened and the fluid intake valve 80 is closed. The inlet pump 66 conveys dialysis solution through the inlet tube 62 from the peritoneal cavity 20 into the membrane device 22. The outlet tube 72 conveys regenerated dialysis solution from the membrane device 22 to the reservoir 88.

When a predetermined pressure condition exists in the reservoir 88, as sensed by the senor 90, the controller 16 switches to the fluid return mode. The inlet pump 66 is stopped. The fluid intake valve 80 is opened, and the fluid removal valve 92 is closed. Regenerated dialysis solution flows by pressure from the reservoir 88 through the outlet tube 72 and into the peritoneal cavity 20. The return mode terminates when the pressure condition in the reservoir 88, as sensed by the sensor 90, drops below a predetermined threshold.

The controller 16 then switches to another fluid draw mode. The controller 16 cycles between successive fluid draw and return modes until the desired objectives of a given therapy session are met.

(C) Subcutaneous Access Device

The system 10 can include one or more subcutaneous access devices 94, which are specially designed to accommodate high flow and frequent cannulation. A dual access arrangement requires two devices 94, whereas a single access arrangement requires but a single device 94.

In the dual access arrangement, the connectors 64 and 74 of the inlet tube 62 and the outlet tube 72 comprise inlet and outlet cannulas. The cannulas are greater than about 18 gauge, and thereby capable of sustaining high flow rates to and from the patient's peritoneal cavity 20. In a single access arrangement, the connector 84 of the connector tube 82 comprises a single cannula.

The cannula connectors, in turn, are inserted into the access devices 94. Each device 94 is implanted subcutaneously for repeated access by the cannula, which is passed into the device 94 percutaneously through the skin.

The access device 94 can be constructed in various ways. In the illustrated embodiment (see FIGS. 3 and 4), the device 94 is generally constructed in the manner disclosed in pending U.S. patent application Ser. No. 08/724,948, filed Nov. 20, 1996, and entitled "Subcutaneously Implanted Cannula and Method for Arterial Access."

Figure 3:
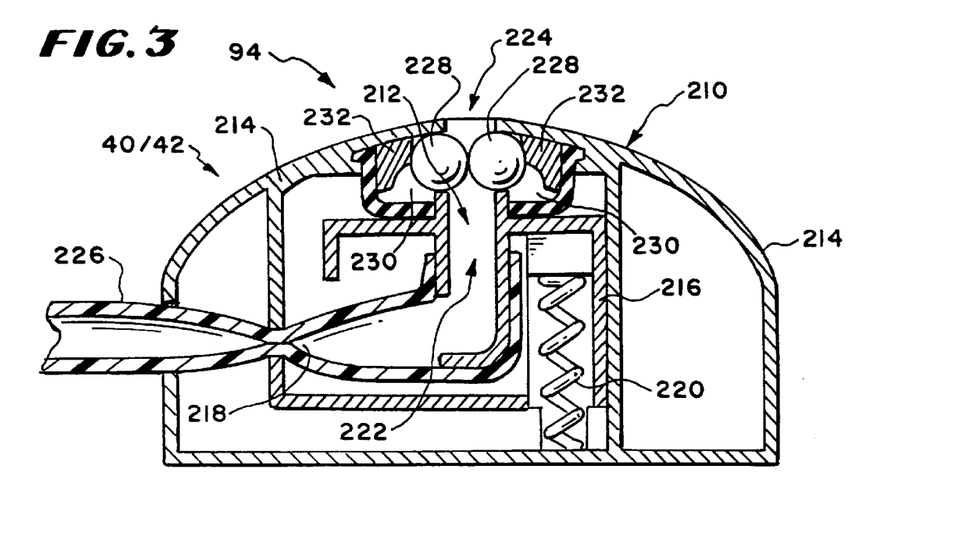
FIG. 3 is a side section view of a subcutaneous peritoneal cavity access device, showing the associated valve assembly in a closed condition.
Figure 4:
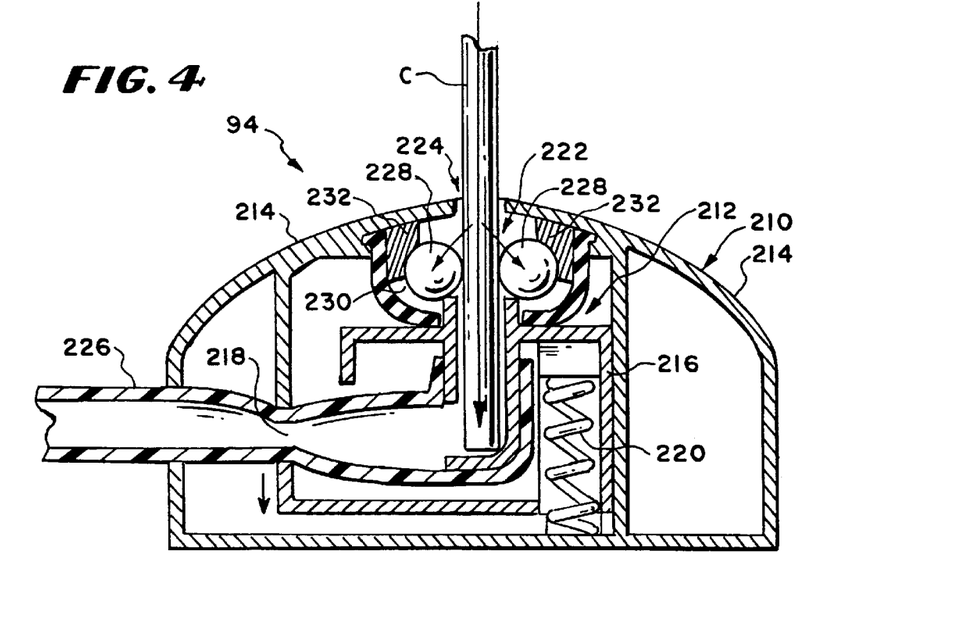
FIG. 4 is a side section view of the subcutaneous peritoneal cavity access device shown in FIG. 3, showing the associated valve assembly in a closed condition.

As shown in FIGS. 3 and 4, the device 94 includes a housing 210 carrying a valve assembly 212. The valve assembly 212 comprises fixed valve member 214 and a shuttle valve member 216.

The shuttle valve member 216 is movable relative to the fixed valve member 214 between opened and closed positions. In the opened position (shown in FIG. 4), the shuttle valve member 216 is spaced away from the fixed valve member 214, forming a valve passage 218 between them. In the closed position (shown in FIG. 3), the shuttle valve member 216 contacts or is in a close adjacent relationship with the fixed valve member 214, which closes the valve passage 218. A spring 220 normally biases the shuttle valve member 216 toward the closed position, shown in FIG. 3.

The device 94 also includes an access passage 222. The access passage 222 opens into the interior of the housing 210 through a port 224. The access passage 222 generally extends perpendicular to the valve passage 218.

A flexible tube 226 is secured to the access passage 222 inside the housing 210. The tube 226 extends from the access passage 222 and bends to pass through the valve passage 218. The tube 226 extends beyond the housing 210 and, when implanted with the device 94, communicates with the peritoneal cavity 20.

As FIG. 3 shows, the normally closed position of the valve assembly 212 pinches the tube 226 between the fixed and movable valve members 214 and 216, thereby blocking fluid flow through the tube 226.

An array of balls 228 rest in a circular channel 230 formed in the access passage 222 near the access port 224. The circular channel 230 allows movement of the balls 228 along a formed cam surface 232 radially of and axially along the access passage 222. Carried with the circular channel 230, the balls 228 rest against the shuttle valve member 216.

The spring 220, which biases the shuttle valve member 216 toward the closed position, also normally urges the balls 228 along the cam surface 232 out into mutually facing contact within the access passage 222 near the access port 224. The surface contact of the balls 228 in this position occurs generally along the center line of the access passage 222 and port 224.

A cannula connector C, when passed through the access port 224 and toward the access passage 222, breaks the surface contact between the balls 228. Continued passage of the cannula connector C between the separated balls 228 and into the access passage 222 causes the balls to move along the cam surface 232 outward of and axially along the passage 222 away from the access port 224. Movement of the balls 228 in this path presses against the shuttle valve member 216.

The cannula connector C transmits through the balls 228 a counter force to the biasing spring 220, which overcomes the spring bias. As a result, the shuttle valve member 216 is moved away from the fixed valve member 214, opening the valve passage 218, as FIG. 4 shows. The tube 226, no longer pinched, opens. Fluid flow through the cannula connector C is directed through the tube 226 to and from the peritoneal cavity 20.

Movement of the cannula connector C out of the access passage 222 relieves the counter force against the balls 228. With the cannula connector C free of the balls 228, the now unopposed biasing force of the spring 220 returns the balls 228 along the cam surface 232 axially toward the access port 224 and radially back into the access passage 222. At the same time, the shuttle valve member 216 is urged toward the closed position, closing the tube 226.

III. Supply of Regeneration Solution (A) Batch Process

The fluid source 40 can provide regeneration solution in a batch process. In this arrangement (see FIG. 5), the fluid source 40 includes a flexible or rigid source container 96. The source container 96 contains an aliquot of purified water from the water treatment module 42 or another source. The aliquot is sufficient to supply regeneration solution for an entire therapy session.

Figure 5:
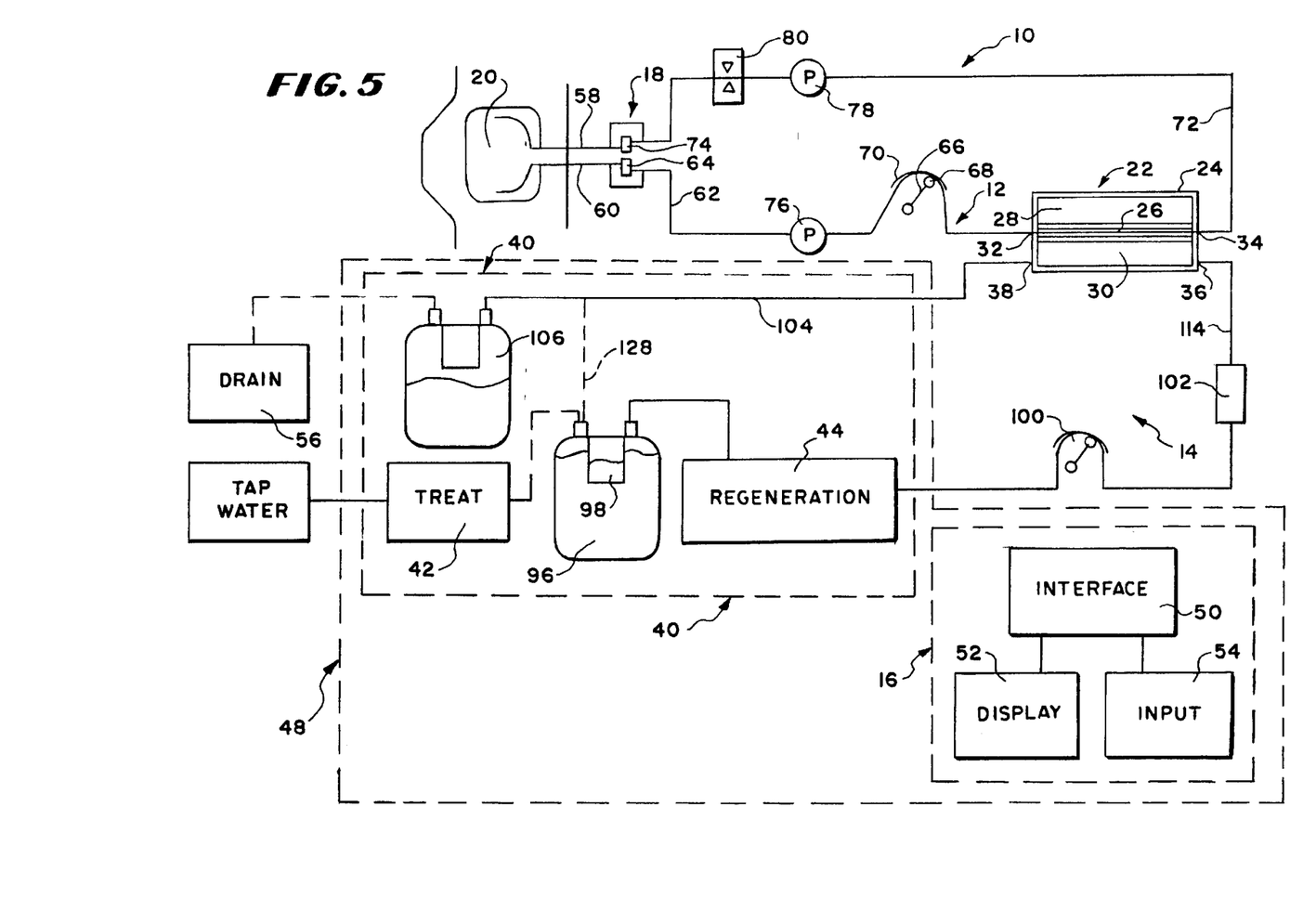
FIG. 5 is a schematic view of a system like that shown in FIG. 1, in which the regeneration solution is supplied in a batch process.

Appropriate electrolytes are added to the purified water in the source container 96. This combination forms the regeneration solution. The appropriate electrolytes can be bicarbonate buffer based or lactate buffer based.

In one embodiment, the appropriate concentration of electrolytes are enclosed within the source container 96 in a smaller bag 98. The bag 98 is made of semi-permeable material. When purified water is introduced into the source container 96, the electrolytes diffuse through the smaller bag 98 into the water, making a homogeneous solution. In another embodiment, the concentrated electrolytes are introduced in powdered or liquid form to the purified water in the source container 96.

The regeneration fluid module 44 draws solution from the source container 96. The module 44 verifies the contents of the solution for safety and heats the solution to body temperature. The module 44 then circulates the regeneration solution to the regeneration side 30 of the membrane device 22, through an inlet line 114 to the port 36, using a pump 100.

If desired, the regeneration solution can be passed through a sterilizing filter 102 prior to entering the regeneration side 30 of the membrane device 22.

A fluid return line 104 communicating with the outlet port 38 on the regeneration side 30 of the membrane device 22 can communicate, via the waste module 46, directly with the drain 56. Alternatively, the fluid return line 104 can be connected to a waste bag 106, which can itself comprise the source container from the previous treatment session.

Still alternatively, the fluid return line 104 can be connected to the source container 96, forming a re-circulation loop 128. The returning used fluid can be separated from the fresh fluid in the source container 96 by a temperature boundary layer, or by a membrane in the source container 96.

(B) Continuous Flow Process

The fluid source 40 can also provide regeneration solution in a continuous flow process. In this arrangement (see FIG. 6), the water treatment module 42 supplies purified water to the regeneration solution module 44 on a continuous or on-demand basis.

Figure 6:
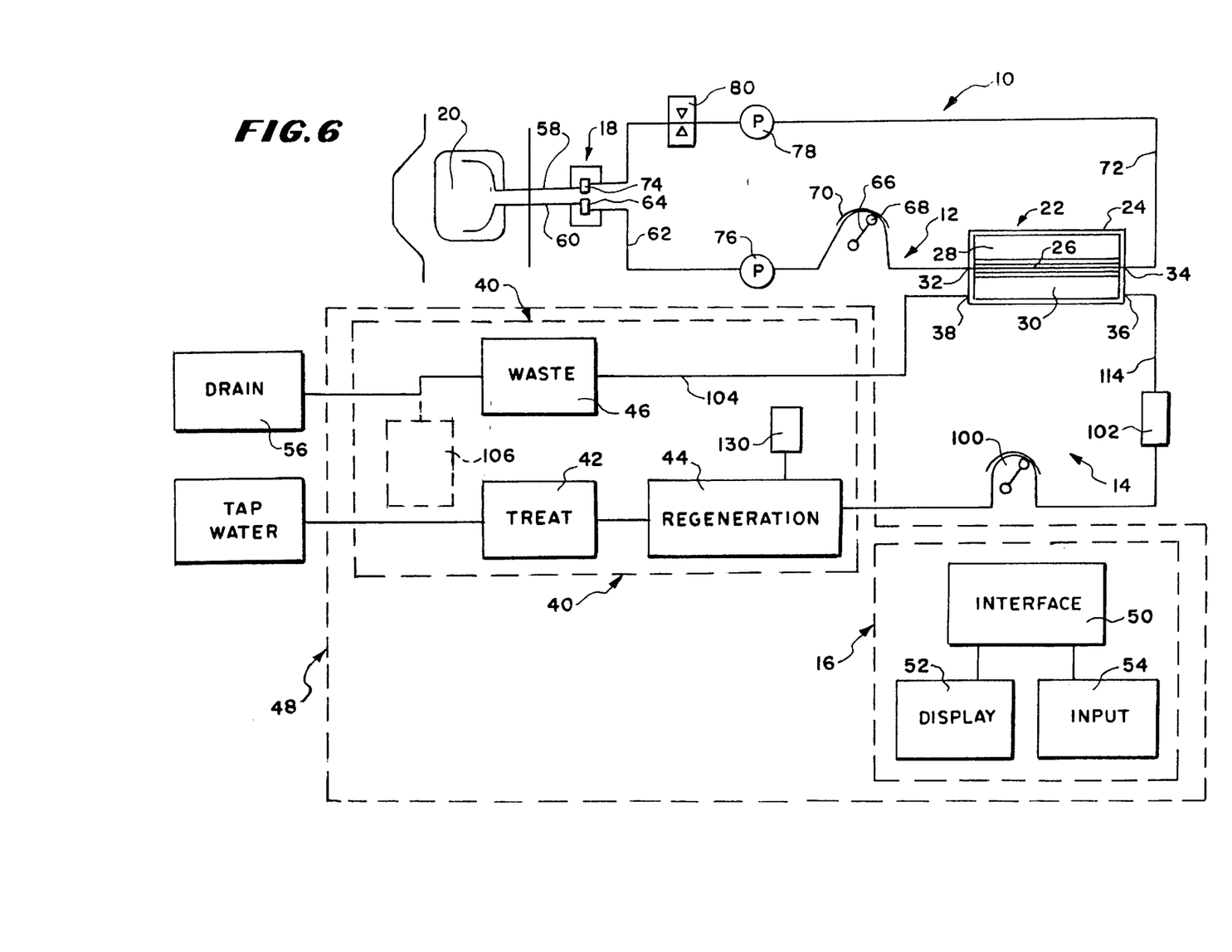
FIG. 6 is a schematic view of a system like that shown in FIG. 1, in which the regeneration solution is supplied in a continuous process.

In this arrangement, the regeneration solution module 44 dispenses the appropriate concentrated electrolyte solution from a source 130 to the purified water to make regeneration solution. As before stated, the appropriate electrolytes can be bicarbonate buffer based or lactate buffer based.

The regeneration solution module 44 verifies the content of the solution for safety and heats the solution to body temperature. The regeneration solution module 44 supplies the solution continuously through the regeneration side 30 of the membrane device 22, through the inlet line 114 to the inlet port 36, using the pump 100. As before stated, the regeneration solution module 44 can pass the solution through the sterilizing filter 102 prior to entering the regeneration side 30 of the membrane device 22.

In this arrangement, as in the batch arrangement, the fluid return line 104, coupled to the outlet port 38 of the regeneration side 30 of the membrane device 22, can be connected to a waste container 106 or directly to a drain 56 through the waste module 46.

IV. Fluid Balancing and Removal

During peritoneal dialysis, it is desirable to maintain, at least partially, a normal physiologic fluid and electrolytic balance in the patient. Usually, an ultrafiltration function is also performed during peritoneal dialysis, by which the overall fluid level of the individual is decreased.

Figure 7:
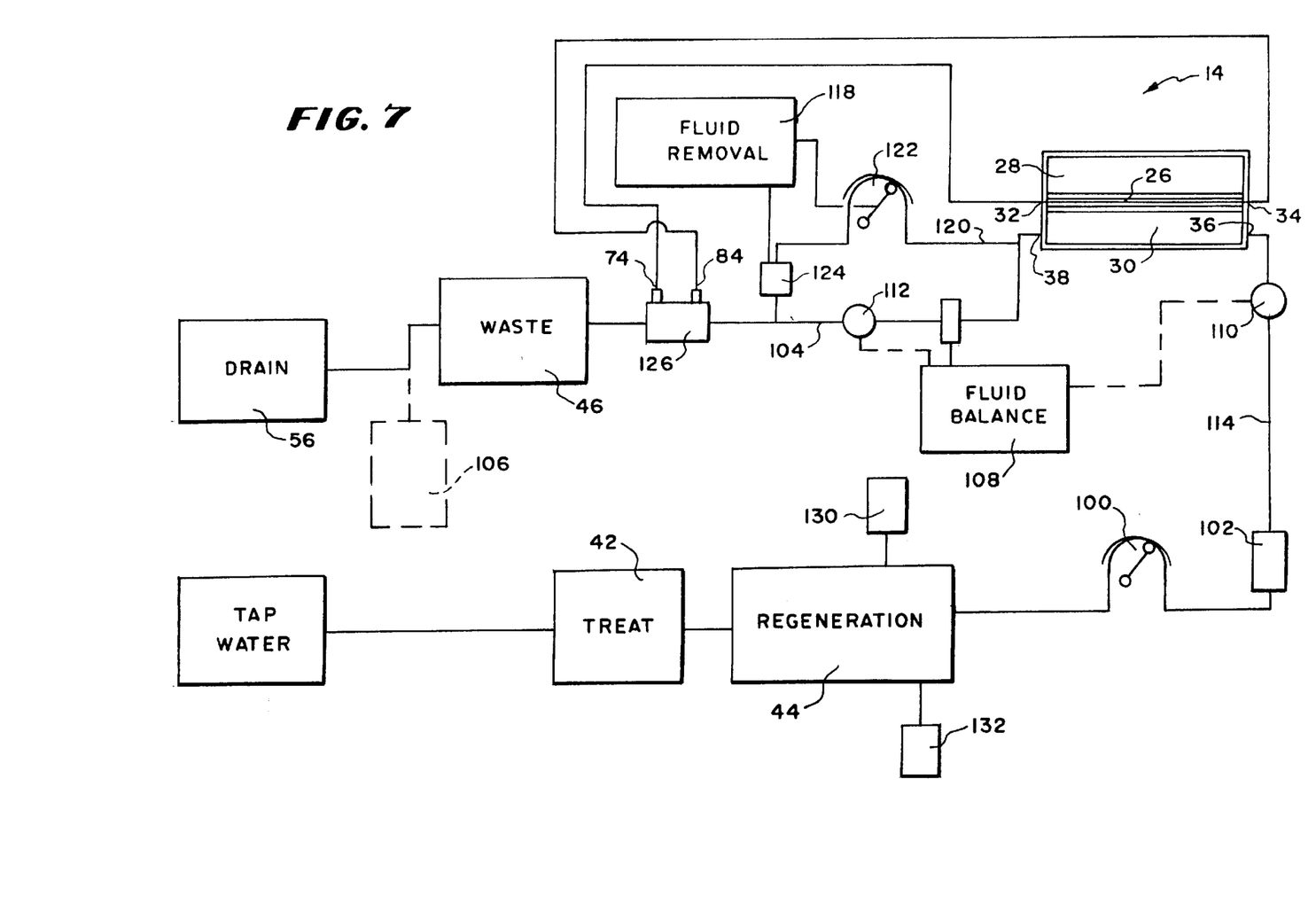
FIG. 7 is a schematic view of the regeneration solution module like that shown in FIG. 1, which also includes fluid balancing and fluid removal capabilities.

For these purposes, the cycler 14 can include a fluid balancing module 108 (see FIG. 7). In the illustrated embodiment, the fluid balancing module 108 includes non-invasive fluid flow rate sensing devices 110 and 112 in the inlet line 114 and the return line 104 of the regeneration side 30 of the membrane device 22.

The fluid balancing module 108 also includes a flow restrictor 116 located in the return line 104. The flow restrictor 116 comprising e.g., a stepper-driven pressure clamp, which pinches the outlet line 104 to control its flow resistance.

The controller 16 monitors the flow rates sensed by the sensing devices 110 and 112. The controller 16 operates the pump 100 and/or the flow restrictor 116 to maintain a zero differential in flow rates at the inlet and outlet of the regeneration side 30 of the membrane device 22. In this way, fluid balance is maintained as the dialysis solution is regenerated.

Other forms of fluid balancing can be used. For example, an outlet pump can be placed in the return line 104, which can be operated in tandem with the inlet pump 100 to achieve fluid balance, without use of in-line pressure sensing. Other flow control devices in the inlet line 114 and return line 104 can be used to achieve a fluid balance between fluid entering and leaving the regeneration side 30 of the membrane device.

There are alternative ways to achieve fluid balancing in a continuous flow arrangement, like that shown in FIG. 7. For example, an outlet pump can be placed in the return line 104, which can be operated in tandem with the inlet pump 100 to achieve fluid balance, without use of in-line pressure sensing. Other flow control devices in the inlet line 114 and return line 104 can be used to achieve a fluid balance between fluid entering and leaving the regeneration side 30 of the membrane device 24.

Fluid balancing can also be achieved in a batch flow arrangement, like that shown in FIG. 5. For example, a pump may be placed in-line in the re-circulation loop 128. The pump is operated in tandem with the pump 100 to achieve fluid balance in the source container 98. Alternatively, without a re-circulation loop 128, a pump can be placed in-line in the return line 104 in the same manner shown in FIG. 7.

To provide an ultrafiltration function, the cycler 14 can also include a fluid removal module 118 (see FIG. 7). In the illustrated embodiment, the fluid removal module 118 includes a fluid removal line 120 and an in-line pump 122 upstream of the flow rate sensor 112 in the outlet line 104. The pump 122 draws additional fluid across the membrane 26 from the dialysis solution, thereby reducing the overall fluid level of the patient.

In the illustrated embodiment, the fluid removal module 118 includes means 124 for monitoring the volume of excess fluid removed. The means 124 can provide a fixed volume measurement chamber, a valve and timing device, or a container with a weight sensing device.

A comparable ultrafiltration function can likewise be achieved in the same manner in the batch flow arrangement shown in FIG. 5.

V. Reuse (A) Reusing the Regeneration Solution Paths

As before described, the portions of the set 12, through which peritoneal dialysis solution flows from and to the patient's peritoneal cavity 20, can be removed from the cycler 14 and disposed of following each treatment. In this arrangement, the tubes through which the regeneration solution flows during the procedure can also be disposed of after treatment.

Alternatively, the fluid source 40 and associated tubes coupled to it can be cleaned and disinfected following each treatment for reuse. In one embodiment, the cleaning and disinfection can be accomplished by flowing heated water, e.g., at 80° C., for, e.g., 1 hour through the fluid source 40 and associated tubes. In another embodiment, the cleaning and disinfection can be accomplished by adding chemicals to water conducted through the fluid source 40 and associated tubes, followed by a water rinse and disinfectant and residual testing.

(B) Reusing the Patient Side Solution Paths

In an alternative embodiment, the portions of the set 12 through which peritoneal dialysis solution flows from and to the patient's peritoneal cavity 20 can themselves be cleaned and disinfected for reuse, along with or independent of the fluid source 40 and associated tubes coupled to it.

In one embodiment, the cleaning and disinfection can be accomplished by connecting the patient connectors 74 and 84 together and circulating hot water (e.g., 80° C.) for, e.g., 1 hour. The remaining electrolytes in the patient side 28 of the fluid pathway will cross the membrane 26 into the water on the regeneration side 30. Circulating hot water through the fluid source 40 and associated tubes on the regeneration side 30 will bring the entire set to a cleaning and disinfecting temperature. After cooling, the regeneration solution side is flushed to remove pyrogenic material. The patient side 28 is likewise flushed with fresh, bagged sterile peritoneal dialysis solution to remove pyrogenic material and to make ready for the next treatment.

In one embodiment, the membrane device 22 in the patient side 28 and the filter 102 in the regeneration side 30 are each pressure tested to determine proper function following heat disinfection.

As an alternative embodiment, the tubing serving the patient side 28 of the membrane device 22 can be removed and disposed of following the cleaning and disinfection process, and replaced with new components.

In an alternative embodiment, a high level disinfectant comprising chemical additives can be circulated through the tubing serving the membrane device 22 or fluid source 40. The disinfectant can be contained in a disinfection container source 132 coupled to the regeneration module 126 (see FIG. 7). The disinfectant in the source 132 is mixed or proportioned into the solution as it is conveyed from the regeneration module 126. During this time, the patient connectors 74 and 84 can be inserted into a shunt container 126, to dispense the disinfectant through the patient side 28 of the membrane device 22 and associated tubes.

The fluid source 40 and associated tubing is disinfected and then rinsed out by purified water, and tested for disinfectant residue. The patient side 28 tubes are flushed are flushed with new, bagged sterile dialysis solution to flush out pyrogenic material and tested for removal of the chemical agents, and to make the system 10 ready for the next treatment.

Various features of the invention are set forth in the following claims.

We claim:

1. A system for conducting peritoneal dialysis comprising a pumping assembly to circulate peritoneal dialysis solution through a peritoneal cavity to perform peritoneal dialysis including a inlet branch to convey peritoneal dialysis solution into the peritoneal cavity and an outlet branch to withdraw peritoneal dialysis solution from the peritoneal cavity, and a regeneration assembly coupled in-line between the inlet and outlet branches, the regeneration assembly including a source of a regeneration solution that carries at least one agent for regenerating spent peritoneal dialysis solution, and a porous membrane having a first side, along which peritoneal dialysis solution is circulated by the pumping assembly from the outlet branch to the inlet branch, and a second side, along which the regeneration solution is circulated, the porous membrane being configured to transport waste from spent peritoneal dialysis solution into the regeneration solution and to transport the regenerating agent from the regeneration solution into spent peritoneal dialysis solution, the regeneration assembly operating to create from peritoneal dialysis solution in the outlet branch, a regenerated dialysis solution for conveyance through the inlet branch into the peritoneal cavity.

2. A system according to claim 1 wherein the regeneration assembly includes a pump to convey regeneration solution from the source along the second side of the porous membrane.

3. A system according to claim 1 wherein the regeneration assembly includes a waste line to remove regeneration solution from the second side of the porous membrane.

4. A system according to claim 3 wherein the waste line communicates with a drain.

5. A system according to claim 3 wherein the waste line communicates with a waste-receiving container.

6. A system according to claim 3 wherein the waste line communicates with the source of regeneration solution to recirculate at least a portion of the regeneration solution.

7. A system according to claim 1 wherein the regenerating agent includes an electrolyte.

8. A system according to claim 1 wherein the regenerating agent includes a buffering agent.

9. A system according to claim 8 wherein the buffering agent comprises a bicarbonate buffering material.

10. A system according to claim 8 wherein the buffering agent comprises a lactate buffering agent.

11. A system according to claim 1 wherein the regenerating agent includes an electrolyte and a buffering agent.

12. A system according to claim 11 wherein the buffering agent comprises a bicarbonate buffering material.

13. A system according to claim 11 wherein the buffering agent comprises a lactate buffering agent.

14. A system according to claim 1 wherein the source of regeneration solution draws water from a source of water.

15. A system according to claim 14 wherein the source of water comprises tap water.

16. A system according to claim 14 wherein the source of regeneration solution includes a device to treat water drawn from the source of water.

17. A system according to claim 14 wherein the source of regeneration solution includes a device to mix the at least one regenerating agent with water drawn from the source of water.

18. A system according to claim 1 wherein the source of regeneration solution draws water from a source of running water.

19. A system according to claim 18 wherein the source of running water is tap water.

20. A system according to claim 18 wherein the source of regeneration solution includes a device to treat water drawn from the source of the running water.

21. A system according to claim 18 wherein the source of regeneration solution includes a device to mix the at least one regenerating agent with water drawn from the source of running water.

22. A system according to claim 1
wherein the source of regeneration solution includes a container holding a volume of water in which the at least one regenerating agent is mixed.

23. A system according to claim 1
wherein the source of regeneration solution includes a first container holding a volume of water and a second container that holds the at least one regenerating agent, the second container being located within the first container and including a wall material that, when contacted by water, transports the at least one regenerating agent into the water, thereby forming the regeneration solution.

24. A system according to claim 1
wherein the regeneration assembly includes a device to heat the regeneration solution before circulation along the second side of the porous membrane.

25. A system according to claim 1
wherein the regeneration assembly includes a sterilizing filter between the source of regeneration solution and the porous membrane.

26. A system according to claim 1
wherein the porous membrane comprises a semipermeable membrane.

27. A system according to claim 26
wherein the porous membrane comprises a bundle of hollow fibers each having an exterior, which comprises the second side of the porous membrane, and an interior lumen, which comprises the first side of the porous membrane.

28. A system according to claim 1
wherein the porous membrane transports waste and the at least one regenerating agent by diffusion, convection, or both.

29. A system according to claim 1
wherein the inlet branch communicates with a first access device providing access to the peritoneal cavity, and
wherein the outlet branch communicates a second access device providing access to the peritoneal cavity independent of the access provided by the first device.

30. A system according to claim 29
wherein the pumping assembly includes a controller that withdraws peritoneal dialysis solution through the second access device into the regeneration assembly while conveying regenerated peritoneal dialysis solution from the regeneration device into the peritoneal cavity through the first access device.

31. A system according to claim 29
wherein at least one of the first and second access devices comprises a subcutaneous access port.

32. A system according to claim 1
wherein the inlet and outlet branches jointly communicate with a single access device that provides common access to the peritoneal cavity.

33. A system according to claim 32
wherein the pumping assembly includes a controller operating in a draw mode, to withdraw peritoneal dialysis solution from the peritoneal cavity through the single access device into the regeneration assembly, and a return mode, to convey regenerated peritoneal dialysis solution into the peritoneal cavity through the single access device.

34. A system according to claim 33
wherein the controller toggles between the draw mode and the return mode.

35. A system according to claim 33
wherein the regeneration assembly includes a reservoir in the inlet branch to collect regenerated peritoneal dialysis solution during the draw mode.

36. A system according to claim 35
wherein the regeneration assembly includes a sensor to sense presence of regenerated dialysis solution in the reservoir and to generate an output relating to volume of regenerated peritoneal dialysis solution present in the reservoir, and
wherein the controller toggles between the draw mode and return mode in response to the output.

37. A system according to claim 32
wherein the single access device comprises a subcutaneous access port.

38. A system according to claim 1
wherein the regeneration assembly includes a fluid balancing module to maintain a volumetric balance between waste and regenerating agent transported by the porous membrane.

39. A system according to claim 1
wherein the regeneration assembly includes an ultrafiltration module to selectively transport a preselected greater volume of waste than regenerating agent.

40. A system according to claim 1
wherein the pumping assembly accommodates circulation of a cleaning or disinfecting agent through the inlet and outlet branches, bypassing the peritoneal cavity.

41. A system according to claim 1
wherein the regeneration assembly accommodates circulation of a cleaning or disinfecting agent along the first and second sides of the porous membrane.

42. A method for conducting peritoneal dialysis comprising steps of
(i) circulating peritoneal dialysis solution through a peritoneal cavity to perform peritoneal dialysis by conveying peritoneal dialysis solution through an inlet branch into the peritoneal cavity and by withdrawing peritoneal dialysis solution through an outlet branch from the peritoneal cavity,
(ii) during at least a portion of step (i), conveying peritoneal dialysis solution in the outlet branch along a first side of a porous membrane while conveying a regeneration solution containing at least one regenerating agent along a second side of the porous membrane, the membrane being configured to transport the regenerating agent into the peritoneal dialysis solution while transporting waste from the peritoneal dialysis solution into the regeneration solution, thereby creating a regenerated peritoneal dialysis solution, and
(iii) during at least a portion of step (i), circulating the regenerated peritoneal dialysis solution through the inlet branch into the peritoneal cavity.

43. A method according to claim 42
wherein steps (ii), and (iii) are performed simultaneously.

44. A method according to claim 42
wherein steps (ii) and (iii) are performed sequentially.

45. A method according to claim 42
wherein, during step (ii), a prescribed volumetric balance is maintained between waste and regenerating agent transported by the porous membrane to achieve fluid balancing.

46. A method according to claim 42
wherein, during step (ii), a preselected greater volume of waste than regenerating agent is selectively transported by the porous membrane to achieve ultrafiltration.

47. A method according to claim 42 wherein, during step (ii), regeneration solution is removed from the second side of the porous membrane to a waste line.

48. A method according to claim 42 wherein, during step (ii), water is drawn from a source of water to create the regeneration solution.

49. A method according to claim 48 wherein the source of water is tap water.

50. A method according to claim 48 wherein, during step (ii), water that is drawn from the source of water is treated.

51. A method according to claim 48 wherein, during step (ii), the at least one regenerating agent is mixed with water drawn from the source of water.

52. A method according to claim 48 wherein, during step (ii), water is drawn from a source of running water to create the regeneration solution.

53. A method according to claim 52 wherein the source of running water is tap water.

54. A method according to claim 52 wherein, during step (ii), water that is drawn from the source of running water is treated.

55. A method according to claim 52 wherein, during step (ii), the at least one regenerating agent is mixed with water drawn from the source of running water.

56. A method according to claim 42 wherein, during step (ii), the regeneration solution is heated before circulation along the second side of the porous membrane.

57. A method according to claim 42 wherein, during step (ii), the regeneration solution is passed through a sterilizing filter before circulation along the second side of the porous membrane.

58. A method according to claim 42 wherein, after completion of step (i), a cleaning or disinfecting agent is circulated through the inlet and outlet branches, bypassing the peritoneal cavity.

59. A method according to claim 42 wherein, after completion of step (i), a cleaning or disinfecting agent is circulated along the first and second sides of the porous membrane.

* * * * *